United States Patent
Pullman et al.

(10) Patent No.: US 6,943,166 B1
(45) Date of Patent: Sep. 13, 2005

(54) COMPOSITIONS COMPRISING PHOSPHODIESTERASE INHABITORS FOR THE TREATMENT OF SEXUAL DISFUNCTION

(75) Inventors: William Ernest Pullman, Far Hills, NJ (US); John Steven Whitaker, Woodinville, WA (US)

(73) Assignee: Lilly ICOS LLC., Wilmington, DE (US)

( * ) Notice: Subject to any disclaimer, the term of this patent is extended or adjusted under 35 U.S.C. 154(b) by 0 days.

(21) Appl. No.: 10/031,556

(22) PCT Filed: Apr. 26, 2000

(86) PCT No.: PCT/US00/11129
§ 371 (c)(1),
(2), (4) Date: Oct. 19, 2001

(87) PCT Pub. No.: WO00/66099
PCT Pub. Date: Nov. 9, 2000

Related U.S. Application Data
(60) Provisional application No. 60/132,036, filed on Apr. 30, 1999.

(51) Int. Cl.[7] ...................... A61K 31/495; A61K 31/50
(52) U.S. Cl. ........................................ 514/250
(58) Field of Search ........................................ 514/250

(56) References Cited

U.S. PATENT DOCUMENTS

| | | | |
|---|---|---|---|
| 5,859,006 A | 1/1999 | Daugan | 514/249 |
| 6,140,329 A * | 10/2000 | Daugan | 514/250 |
| 6,451,807 B1 | 9/2002 | Emmick et al. | |

FOREIGN PATENT DOCUMENTS

| | | | |
|---|---|---|---|
| WO | WO 95/19978 | 7/1995 | ......... C07D/471/14 |
| WO | WO 97/03675 | 2/1997 | ......... A61K/31/495 |
| WO | WO 99 59584 | 11/1999 | |
| WO | WO 99/59584 | 11/1999 | ......... A61K/31/415 |
| WO | WO 00 53148 | 9/2000 | |
| WO | WO 00 66114 | 11/2000 | |
| WO | WO 01 80860 | 11/2001 | |

OTHER PUBLICATIONS

Israel, *The Pharmaceutical Journal*, 261, pp. 164–165 (1998).
Goldenberg, *Clinical Therapeutics*, 20, No. 6, pp. 1033–1048 (1998).
WPIOS AN 2000–339026, Furitsu et al, JP 19990276134, Sep. 1999, abstract.
NDA 20–895 (New Drug Application) Sildenafil for Male Impotence, pp. 99–103 and 183–187, Jan. 22, 1998, author unknown.

* cited by examiner

*Primary Examiner*—Rebecca Cook
(74) *Attorney, Agent, or Firm*—Marshall, Gerstein & Borun LLP

(57) ABSTRACT

The present invention relates to highly selective phosphodiesterase (PDE) enzyme inhibitors and to their use in pharmaceutical articles of manufacture. In particular, the present invention relates to potent inhibitors of cyclic guanosine 3',5'-monophosphate specific phosphodiesterase type 5 (PDE5) that when incorporated into a pharmaceutical product at about 1 to about 20 mg unit dosage are useful for the treatment of sexual dysfunction.

12 Claims, No Drawings

COMPOSITIONS COMPRISING PHOSPHODIESTERASE INHABITORS FOR THE TREATMENT OF SEXUAL DISFUNCTION

CROSS-REFERENCE TO RELATED APPLICATIONS

This is the U.S. national phase application of International Application No. PCT/US00/11129, filed on Apr. 26, 2000, which claims the benefit of provisional patent application Ser. No. 60/132,036, filed Apr. 30, 1999.

FIELD OF THE INVENTION

The present invention relates to a highly selective phosphodiesterase (PDE) enzyme inhibitor and to its use in a pharmaceutical unit dosage form. In particular, the present invention relates to a potent inhibitor of cyclic guanosine 3',5'-monophosphate specific phosphodiesterase type 5 (PDE5) that when incorporated into a pharmaceutical product is useful for the treatment of sexual dysfunction. The unit dosage form described herein is characterized by selective PDE5 inhibition, and accordingly, provides a benefit in therapeutic areas where inhibition of PDE5 is desired, with minimization or elimination of adverse side effects resulting from inhibition of other phosphodiesterase enzymes.

BACKGROUND OF THE INVENTION

The biochemical, physiological, and clinical effects of cyclic guanosine 3',5'-monophosphate specific phosphodiesterase (cGMP-specific PDE) inhibitors suggest their utility in a variety of disease states in which modulation of smooth muscle, renal, hemostatic, inflammatory, and/or endocrine function is desired. Type 5 cGMP-specific phosphodiesterase (PDE5) is the major CGMP hydrolyzing lyzing enzyme in vascular smooth muscle, and its expression in penile corpus cavernosum has been reported (Taher et al., *J. Urol.*, 149, p. 285A (1993)). Thus, PDES is an attractive target in the treatment of sexual dysfunction (Murray, *DN&P* 6(3), pp. 150–56 (1993)).

A pharmaceutical product, which provides a PDE5 inhibitor, is currently available and marketed under the trademark VIAGRA®. The active ingredient in VIAGRA® is sildenafil. The product is sold as an article of manufacture including 25, 50, and 100 mg tablets of sildenafil and a package insert. The package insert provides that sildenafil is a more potent inhibitor of PDE5 than other known phosphodiesterases (greater than 80 fold for PDE1 inhibition, greater than 1,000 fold for PDE2, PDE3, and PDE4 inhibition). The $IC_{50}$ for sildenafil against PDE5 has been reported as 3 rM (*Drugs of the Future*, 22(2), pp. 138–143 (1997)) and as 3.9 nM (Boolel et al., *Int. J. of Impotence*, 8, pp. 47–52 (1996)). Sildenafil is described as having a 4,000-fold selectivity for PDE5 versus PDE3, and only a 10-fold selectivity for PDE5 versus PDE6. Its relative lack of selectivity for PDE6 is theorized to be the basis for abnormalities related to color vision.

While sildenafil has obtained significant commercial success, it has fallen short due to its significant adverse side effects, including facial flushing (10% incidence rate). Adverse side effects limit the use of sildenafil in patients suffering from vison abnormalities, hypertension, and, most significantly, by individuals who use organic nitrates (Welds et al., *Amer. J. of Cardiology*, 83(5A), pp. 21(C)–28(C) (1999)).

The use of sildenafil in patients taking organic nitrates causes a clinically significant drop in blood pressure which could place the patient in danger. Accordingly, the package label for sildenafil provides strict contraindications against its use in combination with organic nitrates (e.g., nitroglycerin, isosorbide mononitrate, isosorbide nitrate, erythrityl tetranitrate) and other nitric oxide donors in any form, either regularly or intermittently, because sildenafil potentiates the hypotensive effects of nitrates. See C. R. Conti et al., *Amer. J. of Cardiology*, 83(5A), pp. 29C–34C (1999). Thus, even with the availability of sildenafil, there remains a need to identify improved pharmaceutical products that are useful in treating sexual dysfunction.

Daugan U.S. Pat. No. 5,859,006 discloses certain tetracyclic derivatives that are potent inhibitors of cGMP-specific PDE, or PDES. The $IC_{50}$ of the compounds disclosed in U.S. Pat. No. 5,859,006 is reported in the range of 1 nM to 10 μM. The oral dosage for such compounds is 0.58 mg daily for an average adult patient (70 kg). Thus, unit dosage forms (tablets or capsules) are reported as 0.2 to 400 mg of active compound. Significant adverse side effects attributed to compounds disclosed in U.S. Pat. No. 5,859,006 are not disclosed.

Applicants have discovered that one such tetracyclic derivative, (6R,12aR)-2,3,6,7,12,12a-hexahydro-2-methyl-6-(3,4-methylenedioxyphenyl)-pyrazino[2',1':6,1]pyrido[3,4-b]indole-1,4-dione, alternatively named (6R-trans)-6-(1,3-benzodioxol-5-yl)-2,3,6,7,12,12a-hexahydro-2-methylpyrazino-[1',2':1,6]pyrido[3,4-b]indole-1,4-dione, and referred to herein as Compound (I), can be administered in a unit dose that provides an effective treatment without the side effects associated with the presently marketed PDE5 inhibitor, sildenafil. Prior to the present invention such side effects were considered inherent to the inhibition of PDE5.

Significantly, applicants' clinical studies also reveal that an effective product having a reduced tendency to cause flushing in susceptible individuals can be provided. Most unexpectedly, the in product also can be administered with clinically insignificant side effects associated with the combined effects of a PDE5 inhibitor and an organic nitrate. Thus, the contraindication once believed necessary for a product containing a PDE5 inhibitor is unnecessary when Compound (I) is administered as a unit dose of about 1 to about 20 mg, as disclosed herein. Thus, the present invention provides an effective therapy for-sexual dysfunction in individuals who previously were untreatable or suffered from unacceptable side effects, including individuals having cardiovascular disease, such as in individuals requiring nitrate therapy, having suffered a myocardial infarction more than three months before the onset of sexual dysfunction therapy, and suffering from class 1 congestive heart failure, or individuals suffering from vision abnormalties.

The present invention provides Compound (I) in a unit dosage form. That is, the present invention provides a pharmaceutical unit dosage form suitable for oral administration comprising about 1 to about 20 mg Compound (I).

SUMMARY OF THE INVENTION

The present invention provides a pharmaceutical dosage form for human pharmaceutical use, comprising about 1 to about 20 mg of (6R,12aR)-2,3,6,7,12,12a-hexahydro-2-methyl-6-(3,4-methylenedioxyphenyl)pyrazino[2',1':6,1]pyrido[3,4-b]indole-1,4-dione in a unit dosage form suitable for oral administration.

The present invention further provides a method of treating conditions where inhibition of PDE5 is desired, which comprises administering to a patient in need thereof an oral dosage form containing about 1 to about 20 mg of a selective PDE5 inhibitor, as needed, up to a total dose of 20 mg per day. The invention further provides the use of an oral dosage form comprising a selective PDE5 inhibitor at a dosage of about 1 to about 20 mg for the treatment of sexual dysfunction.

Specific conditions that can be treated by the present invention, include, but are not limited to, male erectile dysfunction and female sexual dysfunction, particularly female arousal disorder, also known as female sexual arousal disorder.

In particular, the present invention is directed to a pharmaceutical unit dosage composition comprising about 1 to about 20 mg of a compound having the structural formula:

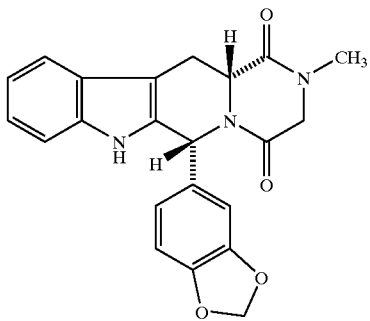

said unit dosage form suitable for oral administration, and method of treating sexual dysfunction using the pharmaceutical unit dose composition.

DETAILED DESCRIPTION

For purposes of the present invention as disclosed and described herein, the following terms and abbreviations are defined as follows.

The term "container" means any receptacle and closure therefor suitable for storing, shipping, dispensing, and/or handling a pharmaceutical product.

The term "$IC_{50}$" is the measure of potency of a compound to inhibit a particular PDE enzyme (e.g., PDE1c, PDE5, or PDE6). The $IC_{50}$ is the concentration of a compound that results in 50% enzyme inhibition in a single dose-response experiment. Determining the $IC_{50}$ value for a compound is readily carried out by a known in vitro methodology generally described in Y. Cheng et al., *Biochem. Pharmacol.*, 22, pp. 3099–3108 (1973).

The term "package insert" means information accompanying the product that provides a description of how to administer the product, along with the safety and efficacy data required to allow the physician, pharmacist, and patient to make an informed decision regarding use of the product. The package insert generally is regarded as the "label" for a pharmaceutical product.

The term "oral dosage form" is used in a general sense to reference pharmaceutical products administered orally. Oral dosage forms are recognized by those skilled in the art to include such forms as liquid formulations, tablets, capsules, and gelcaps.

The term "vision abnormalities" means abnormal vision characterized by blue-green vision believed to be caused by PDE6 inhibition.

The term "flushing" means an episodic redness of the face and neck attributed to vasodilation caused by ingestion of a drug, usually accompanied by a feeling of warmth over the face and neck and sometimes accompanied by perspiration.

The term "free drug" means solid particles of drug not intimately embedded in a polymeric coprecipitate.

The presently claimed dosage form preferably is packaged as an article of manufacture for human pharmaceutical use, comprising a package insert, a container, and a dosage form comprising about 1 to about 20 mg of Compound (I).

The package insert provides a description of how to administer a pharmaceutical product, along with the safety and efficacy data required to allow the physician, pharmacist, and patient to make an informed decision regarding the use of the product. The package insert generally is regarded as the label of the pharmaceutical product. The package insert incorporated into the article of manufacture indicates that Compound (I) is useful in the treatment of conditions wherein inhibition of PDE5 is desired. The package insert also provides instructions to administer one or more about 1 to about 20 mg unit dosage forms as needed, up to a maximum total dose of 20 mg per day. Preferably, the dose administered is about 5 to about 20 mg/day, more preferably about 5 to about 15 mg/day. Most preferably, a 10 mg dosage form is administered once per day.

Preferred conditions to be treated include sexual dysfunction (including male erectile dysfunction; and female sexual dysfunction, and more preferably female arousal disorder (FAD)). The preferred condition to be treated is male erectile dysfunction.

Significantly, the package insert supports the use of the product to treat sexual dysfunction in patients suffering from a retinal disease, for example, diabetic retinopathy or retinitis pigmentosa, or in patients who are using organic nitrates. Thus, the package insert preferably is free of contraindications associated with these conditions, and particularly the administration of the dosage form with an organic nitrate. More preferably, the package insert also is free of any cautions or warnings both associated with retinal diseases, particularly retinitis pigmentosa, and associated with individuals prone to vision abnormalties. Preferably, the package insert also reports incidences of flushing below 2%, preferably below 1%, and most preferably below 0.5%, of the patients administered the dosage form. The incidence rate of flushing demonstrates marked improvement over prior pharmaceutical products containing a PDE5 inhibitor.

The container used in the article of manufacture is conventional in the pharmaceutical Iarts. Generally, the container is a blister pack, foil packet, glass or plastic bottle and accompanying cap or closure, or other such article suitable for use by the patient or pharmacist. Preferably, the container is sized to accommodate 1–1000 solid dosage forms, preferably 1 to 500 solid dosage forms, and most preferably, 5 to 30 solid dosage forms.

Oral dosage forms are recognized by those skilled in the art to include, for example, such forms as liquid formulations, tablets, capsules, and gelcaps. Preferably the dosage forms are solid dosage forms, particularly, tablets comprising about 1 to about 20 mg of Compound (I). Any pharmaceutically acceptable excipients for oral use are suitable for preparation of such dosage forms. Suitable pharmaceutical dosage forms include coprecipitate forms described, for example, in Butler U.S. Pat. No. 5,985,326, incorporated herein by reference. In preferred embodiments, the unit dosage form of the present invention is a solid free of a coprecipitate form of Compound (I), but rather contains solid Compound (I) as a free drug.

Preferably, the tablets comprise pharmaceutical excipients generally recognized as safe such as lactose, microcrystalline cellulose, starch, calcium carbonate, magnesium stearate, stearic acid, talc, and colloidal silicon dioxide, and are prepared by standard pharmaceutical manufacturing techniques as described in *Remington's Pharmaceutical Sciences*, 18th Ed., Mack Publishing Co., Easton, Pa. (1990). Such techniques include, for example, wet granulation followed by drying, milling, and compression into tablets with or without film coating; dry granulation followed by milling, compression into tablets with or without film coating; dry blending followed by compression into tablets, with or without film coating; molded tablets; wet granulation, dried and filled into gelatin capsules; dry blend filled into gelatin capsules; or suspension and solution filled into gelatin capsules. Generally, the solid dosage forms have identifying marks which-are debossed or imprinted on the surface.

The present invention is based on detailed experiments and clinical trials, and the unexpected observations that side effects previously believed to be indicative of PDE5 inhibition can be reduced to clinically insignificant levels by the selection of a compound and unit dose. This unexpected observation enabled the development of a unit dosage form that incorporates Compound (I) in about 1 to about 20 mg per unit dosage forms that, when orally administered, minimizes undesirable side effects previously believed unavoidable. These side effects include facial flushing, vision abnormalities, and a significant decrease in blood pressure, when Compound (I) is administered alone or in combination with an organic nitrate. The minimal effect of Compound (I), administered in about 1 to about 20 mg unit dosage forms, on PDE6 also allows the administration of a selective PDE5 inhibitor to patients suffering from a retinal disease, like diabetic retinopathy or retinitis pigmentosa.

Compound (I) has the following structural formula:

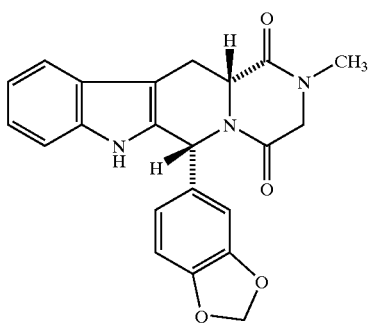

(I)

The compound of structural formula (I) was demonstrated in human clinical studies to exert a minimal impact on systolic blood pressure when administered in conjunction with organic nitrates. By contrast, sildenafil demonstrates a fourfold greater decrease in systolic blood pressure over a placebo, which leads to the contraindications in the VIAGRA insert, and in warnings to certain patients.

The following illustrates the PDE5 and PDE6 $IC_{50}$ values for the compound of structural formula (I) determined by the procedures described herein.

| Compound | PDE5 $IC_{50}$ (nM) | PDE6 $IC_{50}$ (nM) | PDE6/PDE5 |
|---|---|---|---|
| I | 2.5 | 3400 | 1360 |

The compound of structural formula (I) additionally demonstrates an $IC_{50}$ against PDE1c of 10,000, and a ratio of PDE1c/PDE5 of 4,000.

PREPARATIONS

Human PDE5 Preparation

Recombinant production of human PDE5 was carried out essentially as described in Example 7 of U.S. Pat. No. 5,702,936, incorporated herein by reference, except that the yeast transformation vector employed, which is derived from the basic ADH2 plasmid described in V. Price et al., *Methods in Enzymology*, 1985, pages 308–318 (1990), incorporated yeast ADH2 promoter and terminator sequences rather than ADH1 promoter and terminator sequences and the *Saccharomyces cerevisiase* host was the protease-deficient strain BJ2-54 deposited on Aug. 31, 1998 with the American Type Culture Collection, Manassas, Va., under accession number ATCC 74465. Transformed host cells were grown in 2×SC-leu medium, pH 6.2, with trace metals, and vitamins. After 24 hours, YEP medium containing glycerol was added to a final concentration of 2×YEP/3% glycerol. Approximately 24 hours later, cells were harvested, washed, and stored at −700C.

Cell pellets (29 g) were thawed on ice with an equal volume of lysis buffer (25 mM Tris-Cl, pH 8, 5 mM $MgCl_2$, 0.25 mM dithiothreitol, 1 mM benzamidine, and 10 μM $ZnSO_4$). Cells were lysed in a microfluidizer with $N_2$ at 20,000 psi. The lysate was centrifuged and filtered through 0.45 μm disposable filters. The filtrate was applied to a 150 mL column of Q Sepharose Fast Flow (Pharmacia). The column was washed with 1.5 volumes of Buffer A (20 mM Bis-Tris Propane, pH 6.8, 1 mM $MgCl_2$, 0.25 mM dithiothreitol, 10 μM $ZnSO_4$) and eluted with a step gradient of 125 AM NaCl in Buffer A followed by a linear gradient of 125–1000 mM NaCl in Buffer A.

Active fractions from the linear gradient were applied to a 180 mL ceramic hydroxyapatite column in Buffer B (20 mM Bis-Tris Propane (pH 6.8), 1 MM $MgCl_2$, 0.25 mM dithiothreitol, 10 μM $ZnSO_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium-sulfate, and resuspended in Buffer C (20 mM Bis-Tris Propane, pH 6.8, 125 mM NaCl, 0.5 mM dithiothreitol, and 10 μM ZnSO,). The pool was applied to a 140 mL column of Sephacryl S-300 HR and eluted with Buffer C. Active fractions were diluted to 50% glycerol and stored at −20° C. The resultant preparations were about 85% pure by SDS-PAGE.

Assay for PDE Activity

Activity of PDE5 can be measured by standard assays in the art. For example, specific activity of any PDE can be determined as follows. PDE assays utilizing a charcoal separation technique were performed essentially as described in Loughney et al., (1996), *The Journal of Biological Chemistry*, 271:796–806. In this assay, PDE5 activity converts [$^{32}$p]cGMP to [32p]5'GMP in proportion to the amount of PDE5 activity present. The [$^{32}$P]5'GMP then is quantitatively converted to free [$^{32}$P] phosphate and unlabeled adenosine by the action of snake venom 5'-nucleotidase. Hence, the amount of [$^{32}$P] phosphate liberated is proportional to enzyme activity. The assay is performed at 30 C in a 100 μL reaction mixture containing (final concentrations) 40 mM Tris-Cl (pH 8.0), 1 μM $ZnSO_4$, 5 mM MgCl, and 0.1 mg/mL bovine serium albumin. PDE5 is present in quantities that yield <30% total hydrolysis of substrate (linear assay conditions). The assay is initiated by addition of substrate (1 nM [$^{32}$P]cGMP), and the mixture is incubated for 12 minutes. Seventy-five (75) μg of *Crotalus atrox* venom then is added, and the incubation is continued for 3 more minutes (15 minutes total). The reaction is stopped by addition of 200 mL of activated charcoal (25 mg/mL suspension in 0.1 M $NaH_2PO_4$, pH 4). After centrifugation (750 ×g for 3 minutes) to sediment the charcoal, a sample of the supernatant is taken for radioactivity determination in a scintillation counter and the PDE5 activity is calculated. The preparations had specific activities of about 3 μmoles cGMP hydrolyzed per minute per milligram protein.

Bovine PDE6 Preparation

Bovine PDE6 was supplied by Dr. N. Virmaux, INSERM U338, Strasbourg. Bovine retinas were prepared as described by Virmaux et al., *FEBS Letters*, 12(6), pp. 325–328 (1971) and see also, A. Sitaramayya et al., *Exp. Eye Res.*, 25, pp. 163–169 (1977). Briefly, unless stated otherwise, all operations were done in the cold and in dim red light. Eyes were kept in the cold and in the dark for up to four hours after slaughtering.

Preparation of bovine retinal outer segment (ROS) basically followed procedures described by Schichi et al., *J. Biol. Chem.*, 224:529 (1969). In a typical experiment, 35 bovine retinas were ground in a mortar with 35 mL 0.066 M phosphate buffer, pH 7.0, made up to 40% with sucrose, followed by homogenization in a Potter homogenizer (20 up and down strokes). The suspension was centrifuged at 25,000×g for 20 minutes. The pellet was homogenized in 7.5 mL 0.006 M phosphate buffer (40% in sucrose), and carefully layered under 7.5 mL of phosphate buffer (containing no sucrose). Centrifugation was conducted in a swing-out rotor at 45,000×g for 20 minutes, and produced a pellet which is black at the bottom, and also a red band at the interface 0.066 M. phosphate—40% sucrose/0.066 M phosphate (crude ROS). The red material at the interface was removed, diluted with phosphate buffer, spun down to a pellet, and redistributed in buffered 40% sucrose as described above. This procedure was repeated 2 or 3 times until no pellet was formed. The purified ROS was washed in phosphate buffer and finally spun down to a pellet at 25,000×g for 20 minutes. All materials were then kept frozen until used.

Hypotonic extracts were prepared by suspending isolated ROS in 10 mM Tris-Cl pH 7.5, 1 mM EDTA, and 1 mM dithioerythritol, followed by centrifugation at 100,000×g for 30 minutes.

The preparation was reported to have a specific activity of about 35 nmoles cGMP hydrolyzed per minute per milligram protein.

PDE1c Preparation from *Spodoptera fugiperda* Cells (Sf9)

Cell pellets (5g) were thawed on ice with 20 ml of Lysis Buffer (50 mM MOPS pH 7.4, 10 μM $ZnSO_4$, 0.1 mM $CaCl_2$, 1 mM DTT, 2mM benzamidine HCl, 5 μg/ml each of pepstatin, leupeptin, and aprotenin). Cells were lysed by passage through a French pressure cell (SLM-Aminco) while temperatures were maintained below 10° C. The resultant cell homogenate was centrifuged at 36,000 rpm at 4° C. for 45 minutes in a Beckman ultracentrifuge using a Type TI45 rotor. The supernatant was discarded and the resultant pellet was resuspended with 40 ml of Solubilization Buffer (Lysis Buffer containing 1M NaCl, 0.1M $MgCl_2$, 1 mM $CaCl_2$, 20 μg/ml calmodulin, and 1% Sulfobetaine SB12 (Z3-12) by sonicating using a VibraCell tuner with a microtip for 3×30 seconds. This was performed in a crushed ice/salt mix for cooling. Following sonication, the mixture was slowly mixed for 30 minutes at 4° C. to finish solubilizing membrane bound proteins. This mixture was centrifuged in a Beckman ultracentrifuge using a type TI45 rotor at 36,000 rpm for 45 minutes. The supernatant was diluted with Lysis Buffer containing 10 μg/ml calpain inhibitor I and II. The precipitated protein was centrifuged for 20 minutes at 9,000 rpm in a Beckman JA-10 rotor. The recovered supernatant then was subjected to Mimetic Blue AP Agarose Chromatography.

In order to run the Mimetic Blue AP Agarose Column, the resin initially was shielded by the application of 10 bed volumes of 1% polyvinylpurrolidine (i.e., MW of 40,000) to block nonspecific binding sites. The loosely bound PVP-40 was removed by washing with 10 bed volumes of 2M NaCl, and 10 mM sodium citrate pH 3.4. Just prior to addition of the solubilized PDE1c3 sample, the column was equilibrated with 5 bed volumes of Column Buffer A (50 mM MOPS pH 7.4, 10 μM $ZnSO_4$, 5mM $MgCl_2$, 0.1 mM $CaCl_2$, 1 mM DTT, 2 mM benzamidine HCl).

The solubilized sample was applied to the column at a flow rate of 2 ml/min with recycling such that the total sample was applied 4 to 5 times in 12 hours. After loading was completed, the column was washed with 10 column volumes of Column Buffer A, followed by 5 column volumes of Column Buffer B (Column Buffer A containing 20 mM 5'-AMP), and followed by 5 column volumes of Column Buffer C (50 mM MOPS pH 7.4, 10 μM $ZnSO_4$, 0.1 mM $CaCl_2$, 1 mM dithiothreitol, and 2 mM benzamidine HCl). The enzyme was eluted into three successive pools. The first pool consisted of enzyme from a 5 bed volume wash with Column Buffer C containing 1 mM cAMP. The second pool consisted of enzyme from a 10 bed volume wash with Column Buffer C containing 1 M NaCl. The final pool of enzyme consisted of a 5 bed volume wash with Column Buffer C containing 1 M NaCl and 20 mM cAMP.

The active pools of enzyme were collected and the cyclic nucleotide removed via conventional gel filtration chromatography or chromatography on hydroxy-apatite resins. Following removal of cyclic nucleotides, the enzyme pools were dialyzed against Dialysis Buffer containing 25 mM MOPS pH 7.4, 10 μM $ZnSO_4$, 500 mM NaCl, 1 mM $CaCl_2$, 1 mM dithiothreitol, 1 mM benzamidine HCl, followed by dialysis against Dialysis buffer containing 50% glycerol. The enzyme was quick frozen with the aid of dry ice and stored at −70° C.

The resultant preparations were about >90% pure by SDS-PAGE. These preparations had specific activities of about 0.1 to 1.0 μmol cAMP hydrolyzed per minute per milligram protein.

$IC_{50}$ Determinations

The parameter of interest in evaluating the potency of a competitive enzyme inhibitor of PDE5 and/or PDE1c and PDE6 is the inhibition constant, i.e., $K_i$. This parameter can be approximated by determining the ICS,, which is the inhibitor concentration that results in 50% enzyme inhibition, in a single dose-response experiment under the following conditions.

The concentration of inhibitor is always much greater than the concentration of enzyme, so that free inhibitor concentration (which is unknown) is approximated by total inhibitor concentration (which is known).

A suitable range of inhibitor concentrations is chosen (i.e., inhibitor concentrations at least several fold greater and several fold less than the $K_i$ are present in the experiment). Typically, inhibitor concentrations ranged from 10 nM to 10 μM.

The concentrations of enzyme and substrate are chosen such that less than 20% of the substrate is consumed in the absence of inhibitor (providing, e.g., maximum substrate hydrolysis of from 10 to 15%), so that enzyme activity is approximately constant throughout the assay.

The concentration of substrate is less than one-tenth the Michaelis constant ($K_m$). Under these conditions, the $IC_{50}$ will closely approximate the $K_i$. This is because of the Cheng-Prusoff equation relating these two parameters: $IC_{50}=K_i(1+S/K_m)$, with $(1+S/K_m)$ approximately 1 at low values of $S/K_m$.

The $IC_{50}$ value is estimated from the data points by fitting the data to a suitable model of the enzyme inhibitor interaction. When this interaction is known to involve simple competition of the inhibitor with the substrate, a two-parameter model can be used:

$$Y=A/(1+x/B)$$

where the y is the enzyme activity measured at an inhibitor concentration of x, A is the activity in the absence of inhibitor and B is the $IC_{50}$. See Y. Cheng et al., *Biochem. Pharmacol.*, 22:3099–3108 (1973).

Effects of inhibitors of the present invention on enzymatic activity of PDE5 and PDE6 preparations as described above were assessed in either of two assays which differed from each other principally on the basis of scale and provided essentially the same results in terms of $IC_{50}$ values. Both assays involved modification of the procedure of Wells et al., *Biochim. Biophys. Acta*, 384:430 (1975). The first of the assays was performed in a total volume of 200 μl containing 50 mM Tris pH 7.5, 3 mM Mg acetate, 1 mM EDTA, 50 μg/mL snake venom nucleotidase and 50 nM [³H]-cGMP (Amersham). Compounds of the invention were dissolved in DMSO finally present at 2% in the assay. The assays were incubated for 30 minutes at 30° C. and stopped by addition of 800 μl of 10 mM Tris pH 7.5, 10 mM EDTA, 10 mM theophylline, 0.1 mM adenosine, and 0.1 mM guanosine. The mixtures were loaded on to 0.5 mL QAE Sephadex columns, and eluted with 2 mL of 0.1 M formate (pH 7.4). The eluted radioactivity was measured by scintillation counting in Optiphase Hisafe 3.

A second, microplate, PDE assay was developed using Multiscreen plates and a vacuum manifold. The assay (100 μl) contained 50 mM Tris pH 7.5, 5 mM Mg acetate, 1 mM EDTA and 250 μg/mL snake venom nucleotidase. The other components of the reaction mixture were as described above. At the end of the incubation, the total volume of the assays were loaded on a QAE Sephadex microcolumn plate by filtration. Free radioactivity was eluted with 200 μl of water from which 50 μl aliquots were analyzed by scintillatio n counting as described above.

The following examples are presented to further illustrate the preparation of the claimed invention. The scope of the present invention is not to be construed as merely consisting of the following examples.

EXAMPLE 1

Compound (I) was prepared as described in U.S. Pat. No. 5,859,006 and formulated in tablets using wet granulation. Povidone was dissolved in water to make a 10% solution. The active compound, microcrystalline cellulose, croscarmellose sodium, and sodium lauryl sulfate were added to a high shear mixer and mixed for 2 minutes. The powders were wet granulated with the povidone solution and extra water as required to complete the granulation. The resultant mixture was dried in a fluid bed drier with inlet air at 70° C.±5° C. until the loss on drying was below 2.5%. The granules were passed through a Comil with a suitable screen (or a sieve) and added to a suitable mixer. The extragranular croscarmellose sodium and sodium lauryl sulfate, and the colloidal anhydrous silica were passed through a suitable sieve (e.g., 500 micron) and added to the mixer and blended 5 minutes. Magnesium stearate was added and blended for 2 minutes. The blend was compressed to a target compression/weight of 250 mg using 9 mm round normal concave tooling.

The core tablets were coated with an aqueous suspension of Opadry OY-S-7322 using an Accelacota (or similar coating pan) using inlet air at 50° C. to 70° C. until the tablet weight was increased by approximately 8 mg. Opadry OY-S-7322 contains methylhydroxypropylcellulose Ph. Eur., titanium dioxide Ph. Eur., Triacetin USP. Opadry increases the weight of each tablet to about 258 mg. The amount of film coat applied per tablet may be less than that stated depending on the process efficiency.

The tablets are filled into blister packs and accompanied by package insert describing the safety and efficacy of the compound.

| Component | Formulations (mg per tablet) | |
|---|---|---|
| Selective PDE5 Inhibitor[1] | 1 | 5 |
| Hydroxypropyl Methylcellulose Phthalate | 1 | 5 |
| Microcrystalline Cellulose | 221.87 | 213.87 |
| Croscarmellose Sodium | 5.00 | 5.00 |
| Sodium Lauryl Sulfate | 2.50 | 2.50 |
| Povidone K30 | 9.38 | 9.38 |
| Purified Water, USP (water for irrigation) | q.s. | q.s. |
| Croscarmellose Sodium | 5.00 | 5.00 |
| Sodium Lauryl Sulfate | 2.50 | 2.50 |
| Colloidal Anhydrous Silica | 0.50 | 0.50 |
| Magnesium Stearate | 1.25 | 1.25 |
| Total core subtotal | 250.00 | 250.00 |
| (Film coat Opadry OY-S-7322) | about 8 mg | about 8 mg |

[1]Compound (I).

EXAMPLE 2

The following formula is used in preparing the finished dosage form containing 10 mg of Compound (I).

| Ingredient | Quantity (mg) |
|---|---|
| Granulation | |
| Selective PDE5 Inhibitor[1] | 10.00 |
| Lactose Monohydrate | 153.80 |
| Lactose Monohydrate (spray dried) | 25.00 |
| Hydroxypropylcellulose | 4.00 |
| Croscarmellose Sodium | 9.00 |
| Hydroxypropylcellulose (EF) | 1.75 |
| Sodium Lauryl Sulfate | 0.70 |
| | 35.00 |
| Outside Powders | |
| Microcrystalline Cellulose (granular-102) | 37.50 |
| Croscarmellose Sodium | 7.00 |
| Magnesium Stearate (vegetable) | 1.25 |
| Total | 250 mg |
| Film coat (approximately) | 11.25 |

Purified Water, USP is used in the manufacture of the tablets. The water is removed during processing and minimal levels remain in the finished product.

Tablets are manufactured using a wet granulation process. A step-by-step description of the process is as follows. The drug and excipients to be granulated are security sieved. The selective PDE5 inhibitor is dry blended with lactose monohydrate (spray dried), hydroxypropylcellulose, croscarmellose sodium, and lactose monohydrate. The resulting powder blend is granulated with an aqueous solution of hydroxypropylcellulose and sodium lauryl sulfate using a Powrex or other suitable high shear granulator. Additional water can be added to reach the desired endpoint. A mill can be used to delump the wet granulation and facilitate drying. The wet granulation is dried using either a fluid bed dryer or a drying oven. Once the material is dried, it can be sized to eliminate any large agglomerates. Microcrystalline cellulose, croscarmellose sodium, and magnesium stearate are security sieved and added to the dry sized granules. These excipients and the dry granulation are mixed until uniform using a tumble bin, ribbon mixer, or other suitable mixing equipment. The mixing process can be separated into two phases. The microcrystalline cellulose, croscarmellose sodium, and the dried granulation are added to the mixer and blended during the first phase, followed by the addition of the magnesium stearate to this granulation and a second mixing phase.

The mixed granulation then is compressed into tablets using a rotary compression machine. The core tablets are film coated with an aqueous suspension of the appropriate color mixture in a coating pan (e.g., Accela Cota). The coated tablets can be lightly dusted with talc to improve tablet handling characteristics.

The tablets are filled into plastic containers (30 tablets/container) and accompanied by package insert describing the safety and efficacy of the compound.

EXAMPLE 3

The following formula is used in preparing a finished dosage form containing 5 mg of Compound (I).

| Ingredient | Quantity (mg) |
| --- | --- |
| Granulation | |
| Selective PDE5 Inhibitor[1] | 2.50 |
| Lactose Monohydrate | 79.395 |
| Lactose Monohydrate (spray dried) | 12.50 |
| Hydroxypropylcellulose | 2.00 |
| Croscarmellose Sodium | 4.50 |
| Hydroxypropylcellulose (EF) | 0.875 |
| Sodium Lauryl Sulfate | 0.35 |
| Outside Powders | |
| Microcrystalline Cellulose (granular-102) | 18.75 |
| Croscarmellose Sodium | 3.50 |
| Magnesium Stearate (vegetable) | 0.63 |
| Total | 125 mg |
| Film coat (approximately) | 6.875 |

The dosage form of Example 3 was prepared in an identical manner to the dosage form of Example 2.

EXAMPLE 4

| | Solution Capsule | |
| --- | --- | --- |
| Ingredient | mg/capsule | Percent (%) |
| Selective PDE5 Inhibitor[1] | 10 | 2 |
| PEG400 NF | 490 | 98 |
| Fill Weight | 500 | 100 |

The gelatin capsules are precisely filled by pumping an accurate fill volume of pre-dissolved drug formulation into the partially sealed cavity of a capsule. Immediately following injection fill of the drug solution formulation, the capsule is completely heat sealed.

The capsules are filled into plastic containers and accompanied by a package insert.

EXAMPLE 5

This study was a randomized, double-blind, placebo-controlled, two-way crossover design clinical pharmacology drug interaction study that evaluated the hemodynamic effects of concomitant administration of a selective PDE5 inhibitor (i.e., Compound (I)) and short-acting nitrates on healthy male volunteers. In this study, the subjects received either Compound (I) at a dose of 10 mg or a placebo, daily for seven days. On the sixth or seventh day, the subjects received sublingual nitroglycerin (0.4 mg) while supine on a tilt table. The nitroglycerin was administered 3 hours after Compound (I) dosing, and all subjects kept the nitroglycerine tablet under their tongue until it completely dissolved. The subjects were tilted to 70° head-up every 5 minutes for a total of 30 minutes with measurement of blood pressure and heart rate. There were no discontinuations among the twenty-two healthy male subjects (ages 19 to 60 years old) that entered this study.

In a preliminary analysis of this study, Compound (I) was well tolerated and there were no serious adverse events. There were no Compound (I) changes in laboratory safety assessments or 12-lead ECGs. The most common adverse events were headache, dyspepsia, and back pain. Compound (I) demonstrated minimal, if any, effect on mean systolic blood pressure, and mean maximal nitroglycerin-induced decrease in systolic blood pressure.

EXAMPLE 6

In two randomized, double-blinded placebo controlled studies, Compound (I) was administered to patients in need thereof at a range of doses, in both daily dosing and for on demand therapy, for sexual encounters and intercourse in the home setting. Doses from 5 to 20 mg of Compound (I) were efficacious and demonstrated less than 1% flushing and no reports of vision abnormalities. It was found that a 10 mg dose of Compound (I) was fully efficacious and demonstrated minimal side effects.

Enhanced erectile function was determined by the International Index of Erectile Function (IIEF) (Rosen et al., *Urology*, 49, pp. 822–830 (1997)), diaries of sexual attempts, and a global satisfaction question. Compound (I) significantly improved the percentage of successful intercourse attempts including the ability to attain and maintain an erection in both "on demand" and daily dosing regimens.

EXAMPLE 7

A third clinical study was a randomized, double-blind, placebo-controlled study of Compound (I) administered "on demand" to patients with male erectile dysfunction. Compound (I) was administered over a period of eight weeks in the treatment of male erectile dysfunction (ED). Erectile dysfunction (ED) is defined as the persistent inability to attain and/or maintain an erection adequate to permit satisfactory sexual performance. "On demand" dosing is defined as intermittent administration of Compound (I) prior to expected sexual activity.

The study population consisted of 212 men, at least 18 years of age, with mild to severe erectile dysfunction. Compound (I) was orally administered as tablets of coprecipitate made in accordance with Butler U.S. Pat. No. 5,985,326. Compound (I) was administered in 2 mg, 5 mg, 10 mg, and 25 mg doses, "on demand" and not more than once every 24 hours. Treatment with all nitrates, azole antifungals (e.g., ketoconazole or itraconazole), warfarin, erythromycin, or antiandrogens was not allowed at any time during the study. No other approved or experimental medications, treatments, or devices used to treat ED were allowed. Forty-one subjects were administered a placebo.

The two primary efficacy variables were the ability of a subject to penetrate his partner and his ability to maintain an erection during intercourse, as measured by the International Index of Erectile Function (IIEF). The IIEF Questionnaire contains fifteen questions, and is a brief, reliable measure of erectile function. See R. C. Rosen et al., Urology, 49, pp. 822–830 (1997)

Secondary efficacy variables were IIEF domain scores for erectile function, orgasmic function, sexual desire, intercourse satisfaction, and overall satisfaction; the patient's ability to achieve an erection, ability to insert his penis into his partner's vagina, completion of intercourse with ejaculation, satisfaction with the hardness of his erection, and overall satisfaction, all as measured by the Sexual Encounter Profile (SEP) diary; and a global assessment question asked at the end of the treatment period. The SEP is a patient diary instrument documenting each sexual encounter during the course of the study.

The safety aspect of the study included all enrolled subjects, and was assessed by evaluating all reported adverse events, and changes in clinical laboratory values, vital signs, physical examination results, and electrocardiogram results.

At endpoint, patients who rated their penetration ability (IIEF Question 3) as "almost always or always" were as follows: 17.5% in the placebo group, 38.1% in the 2 mg group, 48.8% in the 5 mg group, 51.2% in the 10 mg group, and 83.7% in the 25 mg group. Comparisons revealed statistically significant differences in change in penetration ability between placebo and all dose levels of Compound (I).

At endpoint, patients who rated their ability to maintain an erection (IIEF Question 4) during intercourse as "almost always or always" are as follows: 10.0% in the placebo group, 19.5% in the 2 mg group, 32.6% in the 5 mg group, 39.0% in the 10 mg group, and 69.0% in the 25 mg group. Comparison revealed statistically significant differences in change in penetration ability between placebo and the three higher dose levels of Compound (I).

This study also included a safety evaluation. A treatment-emergent adverse event is defined as a condition not present at baseline that appeared postbaseline, or a condition present at baseline that increased in severity postbaseline. The most commonly reported treatment-emergent adverse events were headache, dyspepsia, and back pain. The incidence of treatment-emergent adverse events appeared related to dose.

Overall, this study demonstrated that all four doses of Compound (I), namely 2 mg, 5 mg, 10 mg, and 25 mg, taken "on demand" produced significant improvement, relative to placebo, in the sexual performance of men with erectile dysfunction as assessed by the IIEF, by patient diaries assessing frequency of successful intercourse and intercourse satisfaction, and by a global assessment.

The combined results from clinical studies showed that administration of Compound (I) effectively treats male erectile dysfunction, as illustrated in the following table.

| IIEF ERECTILE FUNCTION DOMAIN (Change from Baseline) | | | |
|---|---|---|---|
| Unit Dose of Compound (I) | n | Mean ± SD | p |
| placebo | 131 | 0.8 ± 5.3 | |
| 2 mg | 75 | 3.9 ± 6.1 | <.001 |
| 5 mg | 79 | 6.6 ± 7.1 | <.001 |
| 10 mg | 135 | 7.9 ± 6.7 | <.001 |
| 25 mg | 132 | 9.4 ± 7.0 | <.001 |
| 50 mg | 52 | 9.8 ± 5.5 | <.001 |
| 100 mg | 49 | 8.4 ± 6.1 | <.001 | n is number of subjects, SD is standard deviation.

However, it also was observed from the combined clinical studies that the percent of treatment-emergent adverse events increased with an increasing unit dose of Compound (I), as illustrated in the following table:

| Treatment-Emergent Adverse Events (%) | | | | | | | |
|---|---|---|---|---|---|---|---|
| | Unit Dose of Compound (I) (mg) | | | | | | |
| Event | Placebo | 2 | 5 | 10 | 25 | 50 | 100 |
| Headache | 10 | 12 | 10 | 23 | 29 | 34 | 46 |
| Dyspepsia | 6 | 3 | 14 | 13 | 19 | 20 | 25 |
| Back Pain | 5 | 3 | 3 | 15 | 18 | 24 | 22 |
| Myalgia | 3 | 0 | 3 | 9 | 16 | 20 | 29 |
| Rhinitis | 3 | 7 | 3 | 4 | 4 | 0 | 2 |
| Conjunctivitis | 1 | 0 | 1 | 1 | 0 | 2 | 5 |
| Eyelid Edema | 0 | 0 | 0 | 1 | 1 | 2 | 3 |
| Flushing | 0 | 0 | 0 | <1 | 0 | 3 | 7 |
| Vision Abnormalities | 0 | 0 | 0 | 0 | 0 | 0 | 0 |

The above table shows an increase in adverse events at 25 mg through 100 mg unit doses. Accordingly, even though efficacy in the treatment of ED was observed at 25 mg to 100 mg doses, the adverse events observed from 25 mg to 100 mg doses must be considered.

In accordance with the present invention, a unit dose of about 1 to about 20 mg, preferably about 2 to about 20 mg, more preferably about 5 to about 20 mg, and most preferably about 5 to about 15 mg, of Compound (I), administered up to a maximum of 20 mg per 24-hour period, both effectively treats ED and minimizes or eliminates the occurrence of adverse side effects. importantly, no vision abnormalities were reported and flushing was essentially eliminated. Surprisingly, in addition to treating ED, with at about 1 to about 20 mg unit dose Compound (I), with a minimum of adverse side effects, individuals undergoing nitrate therapy also can be treated for ED by the method and composition of the present invention.

The principles, preferred embodiments, and modes of operation of the present invention have been described in the foregoing specification. The invention intended to be protected herein, however, is not construed to be limited to the particular forms disclosed, because they are to be regarded as illustrative rather than restrictive. Variations and changes may be made by those skilled in the art without departing from the spirit of the invention.

What is claimed is:

1. A method of treating sexual dysfunction in a patient in need thereof comprising orally administering one or more unit dose containing about 1 to about 20 mg, up to a maximum total dose of 20 mg per day, of a compound having the structure

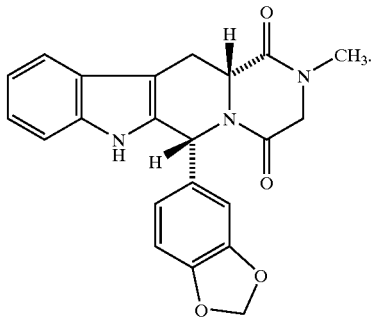

2. The method of claim 1 wherein the sexual dysfunction is male erectile dysfunction.

3. The method of claim 1 wherein the sexual dysfunction is female arousal disorder.

4. The method of claim 1 wherein the unit dose contains about 2 to about 20 mg of the compound.

5. The method of claim 1 wherein the unit dose contains about 5 mg of the compound.

6. The method of claim 1 wherein the unit dose contains about 10 mg of the compound and is administered once per day.

7. The method of claim 1 wherein the unit dose is in a form selected from the group consisting of a liquid, a tablet, a capsule, and a gelcap.

8. The method of claim 1 wherein the unit dose contains about 2.5 mg of the compound.

9. The method of claim 8 wherein the unit dose is administered once per day.

10. The method of claim 5 wherein the unit dose is administered once per day.

11. The method of claim 1 wherein the compound is administered as a free drug.

12. The method of claim 1 wherein the unit dose contains about 20 mg of the compound.

* * * * *

UNITED STATES PATENT AND TRADEMARK OFFICE
CERTIFICATE OF CORRECTION

PATENT NO.       : 6,943,166 B1
APPLICATION NO.  : 10/031556
DATED            : September 13, 2005
INVENTOR(S)      : Pullman et al.

It is certified that error appears in the above-identified patent and that said Letters Patent is hereby corrected as shown below:

First page, line 54, in the title, "INHABITORS" should be --INHIBITORS-- and "DISFUNCTION" should be --DYSFUNCTION--

Column 1, lines 1-4, in the title, "INHABITORS" should be --INHIBITORS-- and "DISFUNCTION" should be --DYSFUNCTION--

Column 1, line 35, "CGMP" should be -- cGMP --

Column 1, line 35, delete "lyzing"

Column 1, line 38, "PDES" should be -- PDE5 --

Column 1, line 51, "3 rM" should be -- 3 nM --

Column 1 line 62, "vison" should be --vision --

Column 2, line 14, "PDES" should be -- PDE5 --

Column 2, line 36, delete "in" between "the" and "product"

Column 2, line 44, "for-sexual" should be -- for sexual --

Column 3, line 45, "in vitro" should be italicized

Column 4, line 45, "Iarts." should be -- arts. --

Column 5, lines 53-54, "VIAGRA" should be -- VIAGRA® --

Column 6, line 15, "2xSC-leu" should be -- 2X SC-leu --

Column 6, line 17, "2xYEP/" should be -- 2X YEP/ --

Column 6, line 19, "-700C." should be -- -70°C. --

Column 6, line 41, "ZnSO,)." should be -- $ZnSO_4$). --

UNITED STATES PATENT AND TRADEMARK OFFICE
CERTIFICATE OF CORRECTION

PATENT NO. : 6,943,166 B1
APPLICATION NO. : 10/031556
DATED : September 13, 2005
INVENTOR(S) : Pullman et al.

It is certified that error appears in the above-identified patent and that said Letters Patent is hereby corrected as shown below:

Column 6, line 53, "[$^{32}$p] cGMP to [32p]5'GMP" should be -- [$^{32}$P] cGMP to [$^{32}$p] 5'GMP --

Signed and Sealed this

Eighth Day of August, 2006

JON W. DUDAS
*Director of the United States Patent and Trademark Office*